United States Patent [19]
Ashton et al.

[11] 4,017,503
[45] Apr. 12, 1977

[54] ANTIFUNGAL 1-SUBSTITUTED BENZIMIDAZOLES
[75] Inventors: Wallace T. Ashton, Clark; Edward F. Rogers, Middletown, both of N.J.
[73] Assignee: Merck & Co., Inc., Rahway, N.J.
[22] Filed: June 12, 1975
[21] Appl. No.: 586,438
[52] U.S. Cl. .............................. 260/302 H; 424/270
[51] Int. Cl.$^2$ ...................................... C07D 417/00
[58] Field of Search ................ 260/302 H; 424/270
[56] References Cited
UNITED STATES PATENTS 3,055,907   9/1962   Brown et al. .................. 260/302 H Primary Examiner—R.J. Gallagher
Attorney, Agent, or Firm—David L. Rose; J. Jerome Behan

[57] ABSTRACT

New benzimidazoles substituted at the 1-position with carbonyl substituents and at the 2-position with a 4-thiazolyl group are effective fungicides and anthelmintics exhibiting particularly useful hydrophilic and lypophilic effects. The compounds as well as processes for their preparation are described along with antifungal and anthelmintic compositions for their use. The 1-position substituent is a loweralkoxy or phenyl-loweralkoxy substituted ethoxy or polyethoxy carbonyl group of a chain with up to 4 ethoxy groups connected to the carbonyl. The compounds are generally prepared by contacting a 1-unsubstituted benzimidazole with a loweralkoxy or phenylloweralkoxy substituted ethoxy or polyethoxy chloroformate.

7 Claims, No Drawings

ANTIFUNGAL 1-SUBSTITUTED BENZIMIDAZOLES

DESCRIPTION OF THE PRIOR ART

Benzimidazoles having a heteroaryl radical in the 2-position have been described in the prior art as anthelmintic and antifungal agents. U.S. Pat. Nos. 3,017,415 and 3,370,957 are illustrative of this prior art. Although these materials are active antifungal agents, the search has continued for substances which are more potent and which are effective against fungi that are non-responsive or weakly responsive to the prior art compounds. In accordance with the present invention there are provided a group of highly active, broad-spectrum antifungal agents.

SUMMARY OF THE INVENTION

This invention relates to new compounds active as fungicides and anthelmintics, and to methods for their use. More specifically, this invention relates to 1-substituted benzimidazoles effective as fungicides which possess a high degree of hydrophilic and lypophilic effects and demonstrate excellent systemic activity in plants and a high degree of mobility in soil. Still more particularly, the invention is directed to novel fungicides comprising compounds described as 1-loweralkoxy or phenylloweralkoxy substituted ethoxy or polyethoxycarbonyl 2-(4-thiazolyl)-benzimidazoles, to compositions containing such compounds and to methods of killing fungi or controlling their growth by the use of such compositions and compounds.

These fungicides are utilized for agricultural application, for instance, in preventing or minimizing fungus growth on plants, fruits, seeds or soil. These fungicidal agents or materials may also find use in medical therapy such as the treatment of mycotic infections of man and animals.

Although many antifungal agents have been described and used heretofore in an effort to control fungi, none are entirely satisfactory and continued losses resulting from fungal attack make the problem of control a serious and lasting one.

It is an object of this invention to provide for novel compounds. It is a further object of this invention to provide novel antifungal agents, which possess a high degree of hydrophilic and lypophilic effects. Another object is to provide for compounds which possess a high degree of systemic activity in plants and a high degree of mobility in soil. It is still a further object of this invention to provide new and improved methods of controlling the growth of fungi. Another object of this invention is to provide compositions useful in the control of fungi in or on plants and animals. It is still a further object of this invention to provide a method for controlling and killing fungi with synthetic organic chemicals. Further objects and advantages will become apparent from the following description of the invention.

As used in the description of our invention the expressions "fungicide" and "fungicidal" are intended to encompass control of fungi broadly so as to include the killing of fungi as well as the inhibiting of growth of fungi.

According to the present invention, it has now been found that certain 1-(substituted carbonyl) benzimidazoles are highly effective antifungal agents. It will be appreciated by those skilled in the art that not all of the compounds defined hereinbelow have exactly the same degree of antifungal activity and it should also be understood that a particular compound of the invention will vary somewhat in activity depending upon the species of fungus subjected to its action.

DESCRIPTION OF THE INVENTION

The novel antifungal active compounds of this invention are best described by the following structural formula:

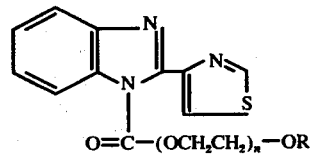

wherein $n$ is a number of from 1 to 4 and R is loweralkyl or phenylloweralkyl.

As employed in the instant invention the term "loweralkyl" is deemed to include those alkyl groups containing from 1 to 5 carbon atoms, either of a straight or branched configuration.

The preferred compounds of this invention are realized when $n$ is 2 to 4 and R is alkyl of from 1 to 3 carbon atoms. Especially preferred are those compounds wherein R is methyl and $n$ is 2 or 4.

As illustrative of the compounds within the scope of this invention, there may be mentioned:

1-(2-benzyloxyethoxycarbonyl)-2-(4-thiazolyl)-benzimidazole 1-(2- { 2-[2-(2-methoxyethoxy)-ethoxy]ethoxy} ethoxycarbonyl)-2-(4-thiazolyl)-benzimidazole or 1-(3,6,9,12-tetraoxa-n-tridecyloxycarbonyl)-2-(4-thiazolyl)-benzimidazole 1-[2-(2-n-butoxyethoxy)ethoxycarbonyl]-2-(4-thiazolyl)-benzimidazole 1-[2-(2-benzyloxyethoxy)ethoxycarbonyl]-2-(4-thiazolyl)-benzimidazole 1-[2-(2-methoxyethoxy)ethoxycarbonyl]-2-(4-thiazolyl)-benzimidazole The compounds of this invention may be employed in fungicidal treatment of seeds and crop seed pieces, plants, fruits, cereal grains, vegetables, nuts, bulbs, corms and tubers, flowers and ornamentals, turf, mushrooms, field crops and soils. These compounds are fungicidally effective against Ascomycetes, such as Erysiphe, Monilinia, Diplodia, Mycosphaerella, Septoria Sclerotinia, *Sphaerotheca spp.* and the llike; Deuteromycetes, (*Fungi imperfecti*), such as Colletotrichum, Botrytis, Fusarium, Penicillium, Verticillium, *Cercospora ssp.*, Rhizoctonia, *Sclerotium spp.*, and the like; and Basidiomycetes such as *Ustilago spp.*, and the like.

The 1-substituted benzimidazoles of this invention are also effective against pathogenic fungi such as *Trichophyton spp.*, *Microsporum spp.*, *Cryptococcus ssp.*, and *Hormodendrum spp.*

These compounds demonstrate particular utility against those fungi which attack plants. They have a high degree of hydrophilic and lypophilic effects and have a surprising and high degree of systemic activity. This causes the instant fungicides to readily mobilize within the plant and to exhibit their effects quickly at the site of the fungal infection. In addition, these fungicides exhibit marked soil mobility, that is they are not bound to the soil and are readily absorbed by the plant's root system into the plant. The soil mobility coupled with the systemic activity and the hydrophilic and lypophilic effects render the instant compounds as particularly useful plant fungicides.

It should be understood that the compounds may be utilized in diverse formulations, solid, including finely divided powders and granular materials as well as liquid, such as solutions, emulsions, suspensions, concentrates, emulsifiable concentrate, slurries and the like, depending upon the application intended and the formulation media desired.

Thus, it will be appreciated that compounds of this invention may be employed to form fungicidally active compositions containing such compounds as essentially active ingredients thereof, which compositions may also include finely divided dry or liquid diluents, extenders, fillers, conditioners and excipients, including various clays, diatomaceous earth, talc, and the like, or water and various organic liquids such as kerosene, benzene, toluene and other petroleum distillate fractions or mixtures thereof.

In general, the compounds of this invention are also effective in combatting superficial mycoses which attack and are an annoyance to humans such as the fungi which causes athletes foot and ringworm.

When the active agents are employed in preventing topical fungal growth one or more of the compounds may be uniformly distributed in a vehicle that is chemically compatible with the particular compound selected, non-inhibiting with respect to the action of the antifungal agent and essentially non-injurious to body tissue under the conditions of use.

It should be understood that the 1-substituted benzimidazoles of the invention may be used in combination one with the other as well as with other fungicidally active materials. For instance, a mixture of 1-substituted benzimidazoles and sulfur, dithiocarbamates, dichlorone, glyodin, dodine, oxine, captan, salicylanilide, dichlorophen, propionates, and mineral oils can be used to give fungicidal effect when used in appropriate concentrations. It is quite clear, too, that the compounds defined according to Formula I above may be used in conjunction with effective antibacterial materials in appropriate instances so as to combine the action of each in such a situation as to be particularly useful, for instance, in applications where the presence of bacteria creates undesirable results alongside the detrimental action of fungi. Accordingly, a combination of antifungal and antibacterial agents will be useful in the preparation of germicidal soaps, and in the production of cosmetics.

The growth of various fungi existing in soil is llimited or terminated by the addition to the soil of minor quantities of the benzimidazole compounds described.

We have also found that the fungicides of the invention are effective against fungal diseases of plants, and may be effectively used either by direct contact with the foliage or systemically, by introduction through the roots.

With respect to the agricultural uses of the fungicides of this invention, the composition may be applied either pre-harvest or post-harvest, depending upon the particular plant, fruit, vegetable or other plant products being treated.

Pre-harvest treatment is used for sugar beets in the treatment of cercospora leaf spot (*Cercospora beticola*). In addition, these compounds are employed in the pre-harvest treatment of soybean pod rot complex, grey mold of grapes and various other fungal diseases of vegetables and field crops. These compounds are of particular value for the control of stem wilt diseases caused by Fusarium and Verticillium species which effect plants such as cotton, tomato and carnation.

Post-harvest treatment of various fruits and vegetables with the compounds of this invention results in the successful treatment of many pathogenic fungi to which the fruit or vegetable is succeptible of infection. Examples are citrus fruits (Penicillium spp., stem end rot organisms and the like); pome fruit such as apples and pears (*Penicillium expansum, Gloeosporium perennans, Botrytis cinerea* and the like); crown rot complex of pathogens of bananas; potato storage and seed piece planting diseases as well as other fungal infections of other fruits and vegetables.

The compounds of this invention also find utility in the various fungi which attack ornamental plants and turf as well as in the treatment of seeds to prevent deterioration due to fungal infection while in storage and after planting.

The pre-harvest treatment of plants with the fungicides of this invention may be carried out using any of the methods known to those skilled in this art. The instant fungicides may be applied as a solution, suspension or dispersion in water in which the plant or the soil in which it is growing, or both, are thoroughly wetted with said aqueous solution, suspension or dispersion. The compounds may be intimately admixed with an inert solid carrier and "dusted" upon the plants. The solid mixture may also contain other necessary ingredients to insure that the composition remains dispersible in air and remains attached to the plant to which it is applied. Or the compounds may be dissolved, suspended or dispersed in a liquid carrier, such as non-phytotoxic oil or other non-aqueous liqud and sprayed directly upon the plant.

When the instant fungicides are used to treat turf and other grasses, the same application methods as above may be employed.

With post-harvest treatment of crops the fungicide may be applied at any time before consumption, preferably just after harvesting. For instance the antifungal compound may be applied during initial storage, before or after shipping or during final storage before consumption. The benzimidazoles of this invention may be utilized in a number of ways to protect the crop from fungal damage. The antifungal benzimidazoles may be applied directly to the crop as a solution, emulsion, suspension, dispersion and the like, in which the carrier vehicle may be aqueous or non-aqueous in the form of a suitable wax, oil, organic solvent and the like. The composition may also contain suitable dispersing agents, stabilizing agents or other material to insure the uniform application of the benzimidazole derivative. Also the antifungal agent may be applied to the container or wrapper within which the crop is kept in order to prevent fungal damage. The antifungal agent is applied to the container or wrapper in carriers and waxes which are known to those skilled in this art.

The compounds of this invention are prepared by contacting 2-(4-thiazolyl)-benzimidazole with a suitable loweralkyl or phenylloweralkyl substituted ethoxy or polyethoxy carbonyl chloride. The carbonyl chloride reagent (also identified as a chloroformate reagent) is prepared by contacting the corresponding alcohol with phosgene. The reaction is outlined in the following reaction scheme:

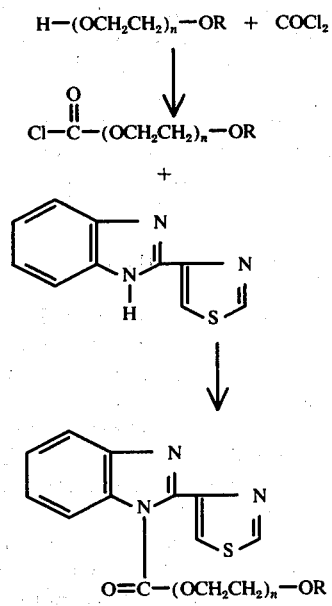

wherein n and R are as previously defined.

The preparation of the chloroformate reagent and its reaction with the benzimidazole are generally conducted in the absence of moisture due to the fact that the product of the first step of the process decomposes in the presence of water. The use of a solvent is not necessary but it is preferred for the operation of this process and when a solvent is used it must be non-reacting with either of the starting materials and the product. Aprotic solvents such as benzene, toluene, xylene, methylene chloride, chloroform, and the like, are among the preferred solvents employed for this process.

The reaction is generally carried out by adding the hydroxy starting material or a solution thereof to a solution of an excess of phosgene gas The reaction is exothermic in nature and external cooling, and prolonged period of the additi on of the starting materials are helpful in moderating the course of the reaction. The initial phase of the reaction is carried out at from −20° to 20° C. during the addition of the hydroxy compound to the phosgene, which may take from 5 minutes to 6 hours, depending on the degree of cooling and the quantity of reactants involved. Following the addition, the reaction mixture is allowed to remain at from 10° to 50° C. for from 1 to 72 hours. Thereafter the reaction is worked up and the product isolated by techniques known to those skilled in this art.

One mole of phosgene is required for each mole of hydroxy compound reacted. However, to assist in the completion of the reaction and to prevent dialkyl carbonate formation, generally an excess of up to 5 equivalents of phosgene is employed. It is preferred to use from 1 to 3 excess moles of phosgene.

In certain cases, it is desirable to include in the reaction mixture an acid acceptor such as an organic base, preferably pyridine, which is present in at least an amount equivalent to the acid liberated during the course of the reaction.

The chloroformate reagent thus prepared is reacted with 2-(4-thiazolyl)-benzimidazole to form the products of structural Formula I. Owing to the reactivity of the chloroformate reagent, the reaction mixture and all of the reagents should be dry. The aprotic solvents previously listed in the description of the preparation of the chloroformate are acceptable for this reaction also. Other solvents may also be employed for this step such as acetonitrile, tetrahydrofuran, dimethyl formamide, and the like.

During the course of the reaction of the chloroformate reagent with the 1-unsubstituted benzimidazole, there is liberated 1 mole of hydrogen chloride. It is preferred to remove the liberated hydrogen chloride from the site of reaction by reacting it with a suitable base. The base must be present to the extent of at least 1 molar equivalent. As bases tertiary amines are preferred such as triethylamine, N,N-diethyl-aniline, pyridine, and the like. Where the base is a liquid which is easily removable at the end of the reaction, the use of a separate solvent may be dispensed with and the base used in such an excess as to become the solvent itself. This technique is especially preferred when pyridine is the acid acceptor. The hydrogen chloride formed during the reaction reacts immediately with the base forming a salt which is removed at the end of the reaction by filtering, dissolving in water or some other technique known to those skilled in this art.

The reaction is run initially at from −10° C. to room temperature owing to the exothermic nature of the reaction. When the reaction subsides after a period of from 5 minutes to 1 hour, the reaction mixture is allowed to come to from 20° to 50° C for 1 to 24 hours to complete the reaction. The product is then isolated and purified by techniques well known to those skilled in this art.

A variation of the above procedure is realized when a metal salt, preferably an alkali metal salt of the 2-(4-thiazolyl)-benzimidazole is prepared prior to its reaction with the chloroformate reagent. Such a salt is prepared by using the alkali metal hydride, hydroxide or loweralkoxide using methods well known in this art. By the use of such a salt of the benzimidazole, the reaction will produce rather than hydrogen chloride, an alkali metal chloride. Thus, with this technique, the use of the base as described above is not needed and it is only necessary to remove the inorganic salt which is formed directly during the course of the reaction.

The process of this reaction is further demonstrated by the following Examples, which Examples are provided for purposes of illustration and are not intended to limit this invention.

EXAMPLE 1

1-[2-(2-methoxyethoxy)ethoxycarbonyl]-2-(4-thiazolyl)-benzimidazole

A. 2-(2-methoxyethoxy)ethyl chloroformate

21 G. of 2-(2-methoxyethoxy)ethanol is added dropwise to 300 ml. of a 12.5% phosgene solution in benzene at a temperature maitained at about 10° C. by immersing the reaction vessel in an ice bath. The reaction mixture is stirred overnight at room temperature. The benzene and the excess phosgene are removed by bubbling nitrogen through the reaction mixture until an oil remained, which is used as is in the next step. Infrared analysis of the oil confirms the structure as 2-(2-methoxyethoxy)ethyl chloroformate.

B. 1-[2-(2-methoxyethoxy)ethoxycarbonyl]-2-(4-thiazolyl)-benzimidazole

The oil from part A is added dropwise to a suspension of 33 g. of 2-(4-thiazolyl)benzimidazole in 400 ml. of pyridine. An exotherm is noted during the addition. The reaction mixture is alowed to stand at room temperature for 16 hours. The reaction mixture is filtered and the solid material suspended in methylene chloride and washed with 3 portions of 2.5 N. hydrochloric acid solution, followed by 2 portions of water. The methylene chloride solution is dried, treated with charcoal, and evaporated to dryness in vacuo affording 36 g. of 1-[2-(2-methoxyethoxy)ethoxycarbonyl]-2-(4-thiazolyl)benzimidazole. The structure is confirmed by infrared analysis.

EXAMPLE 2

1-[2-(2-n-Butoxyethoxy)ethoxycarbonyl]-2-(4-thiazolyl)-benzimidazole

A. 2-(2-n-butoxyethoxy)ethyl chloroformate 24.3 G. (150 mmoles) of 2-(2-n-butoxyethoxy)ethanol is added dropwise with stirring to 250 ml. (290 mmoles) of a 12.5% phosgene solution in benzene, cooled in an ice bath and protected from moisture. The addition is carried out over a period of approximately 1 ½ hours and stirring is continued in an ice bath for 2 hours. The solution is allowed to warm to room temperature and stirred overnight. Nitrogen is passed through the solution for several hours to remove excess phosgene and excess HCl. The solvent is removed in vacuo affording 32.9 g. of a colorless oil. The infrared spectrum revealed a strong carbonyl absorption and no hydroxy absorption. The oil is used without any further purification in the next step.

B. 1-[2-(2-n-Butoxyethoxy)ethoxycarbonyl]-2-(4-thiazolyl)-benzimidazole 32.9 G. (146 mmoles) of 2(2-n-Butoxyethoxy)-ethyl chloroformate is added dropwise to a stirred suspension of 24.9 g. (124 mmoles) of 2-(4-thiazolyl)-benzimidazole in 200 ml. of pyridine. The addition is complete in 40 minutes whereupon all of the starting material had dissolved. The reaction mixture is stirred for 16 hours at room temperature and filtered to remove pyridine hydrochloride which is washed with additional pyridine. The combined filtrate and washing are evaporated to dryness in vacuo affording a residual oil which is triturated with 300 ml. portions of ice water. The water is decanted and the residue extracted with 300 ml. of methylene chloride, filtered and the methylene chloride filtrates washed with 300 ml. of ice water, 250 ml. of 0.25 N HCl containing ice and 200 ml. of saturated sodium bicarbonate solution containing 50 ml. of ice. The organic fraction is dried, filtered and evaporated to dryness in vacuo affording 51.7 g. of a residual oil. The oil is extracted with petroleum ether whereupon a dark oil remains. The petroleum ether solution is decanted and the product separates therefrom as an oil. The petroleum ether is decanted and the remaining solvent is removed in vacuo affording 17.4 g. of a light yellow residual oil. Thin layer chromatography revealed a single spot which is confirmed by elemental analysis.

EXAMPLE 3

1-(2-Benzyloxyethoxycarbonyl)-2-(4-thiazolyl)-benzimidazole

A. 2-benzyloxyethyl chloroformate 22.7 G. (150 mmoles) of 2-benzyloxyethanol is added dropwise with stirring to 188 ml. (300 mmoles) of a 17.2% phosgene solution in benzene cooled in an ice bath with protection from moisture. The addition is complete in 40 minutes and the solution is stirred in the ice bath for an additional hour. The reaction mixture is allowed to warm to room temperature and stirred overnight. A stream of nitrogen is passed through the solution to remove the excess phosgene and HCl. The reaction mixture is evaporated to dryness in vacuo affording 32.2 g. of a light orange residual oil. Infrared analysis reveals a strong carbonyl absorption and minimal hydroxy absorption. The material is used as is in the next step.

B. 1-(2-Benzyloxyethoxycarbonyl)-2-(4-thiazolyl)-benzimidazole 32.2 G. (150 mmoles) of 2-benzyloxyethylchloroformate is added dropwise with protection from moisture to a stirred suspension of 30.1 g. (150 mmoles) of 2(4-thiazolyl)-benzimidazole in 200 ml. of pyridine. The addition is complete in 30 minutes whereupon all of the starting material is dissolved and pyridine hydrochloride begins to precipitate. The reaction mixture is stirred at room temperature for 15 ½ hours and filtered to remove pyridine hydrochloride. The solid material is washed with a small volume of pyridine and the combined filtrate and washing are evaporated to dryness in vacuo. The residual oil is dissolved in 300 ml. of methylene chloride and allowed to stand during which time a substantial amount of solid material precipitates. The solid is removed by filtration and the filtrate washed twice with 250 ml. of 0.25 N HCl containing ice followed by 200 ml. of saturated sodium bicarbonate solution containing 50 ml. of ice. The methylene chloride fraction is dried with magnesium sulfate, treated with charcoal, filtered and evaporated to dryness in vacuo affording 38.9 g. of a yellow-orange oil which begins to solidify on standing. The material is recrystalized from toluenecyclohexane affording 23.8 g. of 1-(2-benzyloxyethoxycarbonyl)-2-(4-thiazolyl)-benzimidazole, m.p. 93°–95° C.

EXAMPLE 4

1-(2-{2-[2-(2-methoxyethoxy)-ethoxy]-ethoxy}-ethoxycarbonyl)-2(4-thiazolyl)-benzimidazole A. Tetraethylene glycol monomethyl ether chloroformate A mixture of 12.9 g. (62 mmoles) of tetraethylene glycol monomethyl ether and 4.9 g. (62 mmoles) of pyridine is added dropwise to 77 ml. (124 mmoles) of a 17.2% solution of phosgene in benzene stirred in an ice bath with protection from moisture. The pyridine hydrochloride precipitates during the 35 to 40 minute addition and stirring is continued in the ice bath for an additional 2 hours. The reaction mixture is allowed to warm to room temperature and stirred overnight. The benzene solution is decanted from the pyridine hydrochloride which is washed with additional benzene. A stream of nitrogen is passed through the solution to remove excess phosgene as well as most of the benzene. The residual oil is dissolved in benzene-hexane and filtered to remove additional pyridine hydrochloride. The filtrate is evaporated to dryness in vacuo affording 17.1 g. of a residual oil, the infrared analysis of which reveals a strong carbonyl absorption and minimal hydroxyl absorption. The oil is used as is in the next step.

B. 1-(2-{2-[2-Methoxyethoxy)-ethoxy]-ethoxy}-ethoxycarbonyl-2-(4-thiazolyl)benzimidazole To a stirred suspension of 12.4 g. (62 mmoles) of 2-(4-thiazolyl)-benzimidazole in 100 ml. of pyridine is added dropwise 17.1 g. (62 mmoles) of tetraethylene glycol monomethyl ether chloroformate with protection from moisture over a period of 30 minutes. During the addition, the starting material dissolves and pyridine hydrochloride begins to precipitate. The reaction mixture is stirred for 18 hours at room temperature and filtered. The filtrate is evaporated to dryness in vacuo and the residual oil dissolved in 200 ml. of methylene chloride. The methylene chloride is filtered, washed twice with 150 ml. of 0.25 N HCl containing ice and 100 ml. of saturated sodium bicarbonate solution containing 50 ml. of ice. The methylene chloride fraction is dried with magnesium sulfate treated with charcoal and filtered and evaporated to dryness in vacuo affording 21.9 g. of a light yellow-orange residual oil. The infrared analysis reveals a strong carbonyl absorption and the structure is confirmed by elemental analysis.

When the compounds of this invention are employed in compositions useful for the destruction of fungi or the prevention of the growth fungi, the active ingredient is present to an extent which depends greatly upon the method of application of the antifungal agent. Concentrations ranging from 200 to 5000 parts per million may be employed.

These compositions are applied to the plant, plant product, soil, or other objects where fungal growth is present or suspected. In addition to applying these compositions to existing or suspected sites of fungal infection, it is very often useful to apply said compositions to plants, plant products, soil or other objects where there is no fungal infection, however, from past experiences, fungal infections could reasonably be predicted. An example would be the treatment of fruits or vegetables which contain no fungal infection but which are to be placed in storage for prolonged periods or for shipment. In such situations, experience has shown that, left untreated, the fruits and vegetables will develop fungal infections, Treatment of such fruits and vegetables prior to storage will prevent the development of such fungal infections.

The above concentrations of active ingredient are descriptive of those compositions which are to be applied directly to the site of fungal infection, suspected fungal infection or sites where fungal infection is predicted. However, it may be desired to provide for an intermediate composition of the compounds of this invention wherein the active ingredient is present to the extent of from 1 to 90% by weight. The remaining ingredients are auxiliary agents such as fillers, excipients, binders or other inert ingredients necessary to maintain the integrity of the composition. This higher concentration composition is further diluted, with the proper diluent for the particular contemplated use, prior to such use. The dilution brings the concentration of the active ingredient to that desired or necessary for the particular use to which the antifungal composition is to be put.

Compositions containing the active ingredient of structural Formula I are active against various fungi when such composition is applied to an area, plant or animal in which fungal growth is present, suspected, or predicted.

In one such example in a greenhouse test an aqueous solution containing from 0.25 to 1% acetone and 7.5, 15 or 30 parts per million of the active compound was applied as a spray until runoff to young bean plants which had been previously inoculated with powdery mildew (*Erysiphe Polygoni*). Other plants were left untreated as controls. It is noted that field applications (as opposed to this laboratory situation) utilize a much higher level of active compound (200 to 5000 ppm.). In the laboratory situation care is taken to thoroughly wet the entire surface of all the leaves of the plant. Since such techniques are too time consuming for field use, higher concentrations are employed. After 5 to 7 days the plants were evaluated on a scale of from 0 to 10 with 0 being no fungal infection and 10 being complete fungal infection. Scores of from 0 to 2 are considered as adequate control. In such tests, the untreated plants were completely infected with the fungus while the instant compounds, at concentrations of 15 or 30 ppm., afforded adequate control.

When the compounds of this invention are intended for topical use such as in a cream or ointment, a base therefor is employed in which the active compound is present at a concentration of from 0.01% to 15% preferably from about 0.5% to 10% (percentages are by weight).

In addition to their antifungal activity, the compounds of this invention have significant activity as anthelmintics thus being useful in the treatment of helminthiasis in animals. The disease or group of diseases described generally as helminthiasis is due to infestation of the animal body with parasitic worms known as helminths. Helminthiasis is a prevalent and serious economic problem in domesticated animals such as swine, sheep, cattle, goats, dogs and poultry. Among the helminths, the group of worms described as nematodes causes widespread and often serious infection in various species of animals. Certain species of nematodes also lead to troublesome infections in humans, particularly in the tropical climates. The parasitic infections known as helminthiasis lead to anemia, malnutrition, weakness, weight loss, severe damage to the walls of the intestinal tract and, if left untreated, often result in death of the infected animals. The compounds of this invention have unexpectedly high activity against these helminths.

When used as anthelmintic agents, they may be administered orally in a unit dosage form such as a capsule, bolus, tablet or as a liquid drench. Alternatively, the anthelmintic compounds of this invention may be administered to animals by intraruminal, intramuscular and intratracheal injection, in which event the benzimidazole is dissolved or dispersed in a liquid carrier vehicle.

The optimum amount of the active agent to be employed for best results will, of course, depend upon the particular benzimidazole employed, the species of animal to be treated and the type and severity of helminth infection. Generally, good results are obtained with the compounds of this invention by the oral administration of from about 5 to 125 mg. per kg. of animal body weight, such total dose being given at one time or in divided does over a relatively short period of time such as 1–2 days. With the preferred compounds of the invention, excellent control of helminthiasis is obtained in domesticated animals by administering from about 10 to 70 mg. per kg. of body weight in a single dose. The techniques for administering these materials to animals are known to those skilled in the veterinary field.

What is claimed is:
1. A compound having the formula:

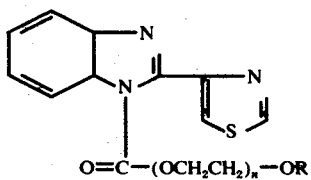

wherein *n* is a number of from 1 to 4; and R is loweralkyl or phenylloweralkyl.

2. The compound of claim 1 wherein *n* is a number of from 2 to 4 and R is alkyl.

3. The compound of claim 1 wherein R is methyl and *n* is 2 or 4.

4. The compound of claim 1 which is 1-(2-benzyloxyethoxycarbonyl)-2-(4-thiazolyl)-benzimidazole.

5. The compound of claim 1 which is 1-[2-(2-n-butoxyethoxy)ethoxycarbonyl]-2-(4-thiazolyl)-benzimidazole.

6. The compound of claim 1 which is 1-(2-{2-[2-(2-methoxyethoxy)ethoxy]ethoxy} ethoxycarbonyl)-2-(4-thiazolyl)-benzimidazole.

7. The compound of claim 1 which is 1-[2-(2-methoxyethoxy)ethoxycarbonyl]-2-(4-thiazolyl)-benzimidazole.

* * * * *